United States Patent [19]

Yataki et al.

[11] 4,097,160

[45] Jun. 27, 1978

[54] METHOD FOR INSPECTING OBJECT DEFECTION BY LIGHT BEAM

[75] Inventors: Masamichi Yataki, Tama; Hideyo Takahata, Yokohama; Norio Simomura, Kawasaki, all of Japan

[73] Assignee: Canon Kabushiki Kaisha, Tokyo, Japan

[21] Appl. No.: 784,328

[22] Filed: Apr. 4, 1977

Related U.S. Application Data

[63] Continuation of Ser. No. 609,945, Sep. 3, 1975, abandoned.

[30] Foreign Application Priority Data

Oct. 7, 1974 Japan .............................. 49-115323
Oct. 2, 1974 Japan .............................. 49-113610
Sep. 6, 1974 Japan .............................. 49-1102679

[51] Int. Cl.² ...................... G01N 21/32; G01N 21/48
[52] U.S. Cl. ................................. 356/237; 250/563; 250/572; 356/200; 356/210

[58] Field of Search ............... 356/200, 210, 237; 250/563, 572

[56] References Cited

U.S. PATENT DOCUMENTS 3,280,692  10/1966  Milnes et al. ..................... 356/200
3,834,822  9/1974  Stapleton et al. ................. 356/200

*Primary Examiner*—Vincent P. McGraw
*Attorney, Agent, or Firm*—Toren, McGeady and Stanger

[57] ABSTRACT

A narrow beam from a laser source-like light beam is projected on an object, the light scattered from the projected spot of the object is detected by light detecters at a plural number of the detecting positions. The distribution of the scattered light is detected by comparing the values of the densities of the scattered lights at the plural number of the detecting positions among each other in such a manner that it is determined from the distribution of the scattered light whether there is a defect on the projected spot or not.

1 Claim, 28 Drawing Figures

(a)

(b)

(c)

(a)

(b)

(c)

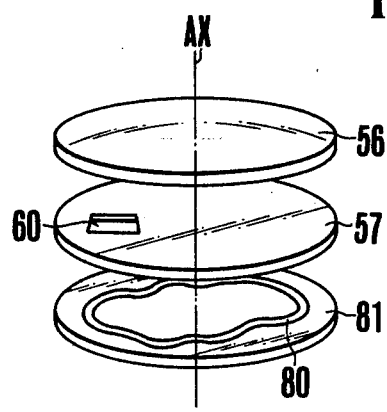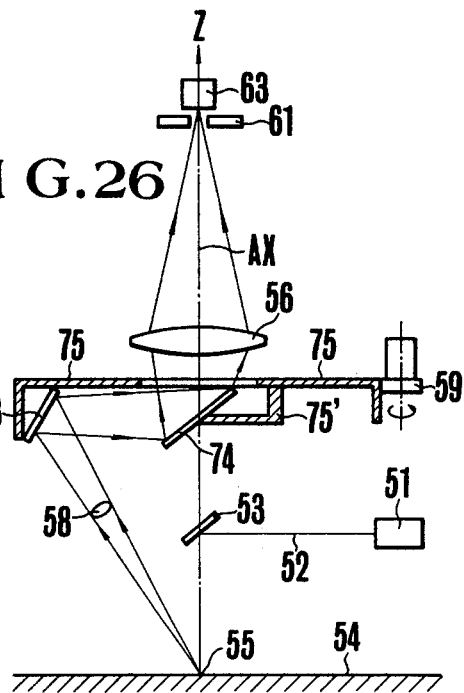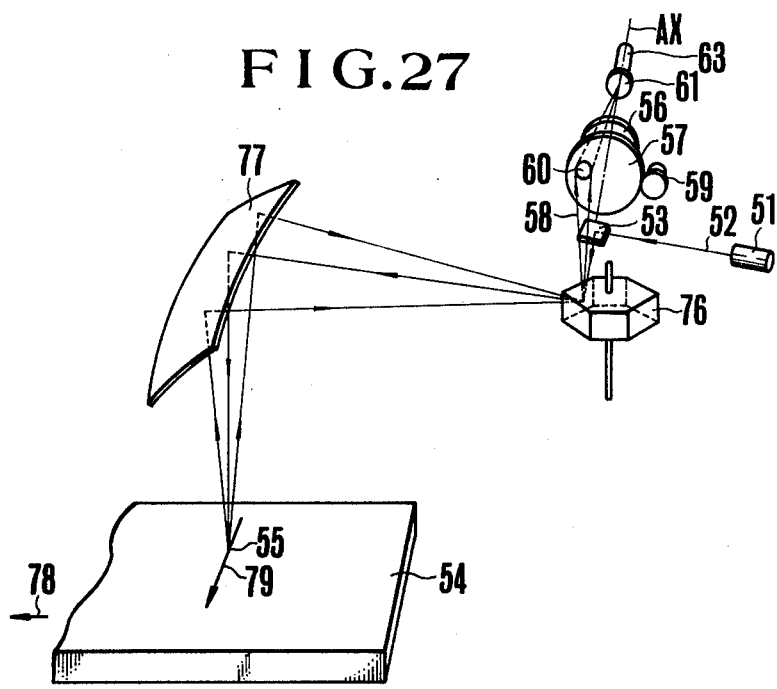

METHOD FOR INSPECTING OBJECT DEFECTION BY LIGHT BEAM

This is a continuation of application Ser. No. 609,945 filed Sept. 3, 1975, now abandoned.

BACKGROUND OF THE INVENTION

The present invention relates to a method for optically inspecting an object defect.

Hereby the object defect means scratches, stains on the surface of the object, cavities in the object and alien mixture in the particles as is mentioned in U.S. Pat. No. 3,549,263 and so on.

In the conventional method for optical inspection, for example, as is disclosed in U.S. Pat. No. 2,719,235, the object is scanned by means of a narrow light beam, whereby the light scattered from the scanned spots is received by a single light detecting means in such a manner that it is judged from the variation of the output of the light detecting means whether there is a defect or not.

In other words, it is determined from the difference between the amount of the light scattered from a scanned spot on the object and that of the light scattered from another scanned spot following the first scanned spot whether there is a defect or not. Hereby, the scanned spot means the portion on the object on which the scanning beam is projected. As a consequence, the scanned spot moves with the movement of the scanning beam.

SUMMARY OF THE INVENTION

The inspection method in accordance with the present invention is a new one, quite different from the above mentioned conventional one.

Namely, the light scattered from the scanned spot (projected spot) is detected by means of the light detectors at a plural number of the detecting positions, the distribution of the scattered light is detected by comparing the values of the densities of the scattered lights at the plural number of the detecting positions among each other and it is decided from a comparison of the distribution of the scattered light with that of the light scattered from the scanned spot without defect whether there is a defect or not.

In other words, by means of the inspection method in accordance with the present invention, the direction of the principal axis of the light beam scattered from each scanned spot is detected in such a manner that it is decided from the comparison of the detected direction of the axis with that of the light beam scattered from the scanned spot without defect whether there is a defect or not.

Hereby the principal axis of the scattered light beam means a light beam which forms a peak in the density distribution of the scattered light in an optional plane crossing the scattered light beam while the direction of principal axis of the scattered light beam is the direction along which the light beam forming the above mentioned peak propagates.

The reason why defects and so on can be detected by detecting the direction of the principal axis of the scattered light beam is that the direction of the principal axis of the scattered light beam is deviated by the defects and so on. For example, it can easily be understood that in case there is a projecting defect presenting an inclination on the surface to be inspected, the direction of the principal axis of the scattered light beam is deviated by the projecting defect.

The direction of the principal axis of the scattered light beam can be detected by comparing the outputs of a substantially plural number of the light sensing elements disposed with a certain determined distance from each other in the scattered light beam among each other. Hereby a substantially plural number of the light sensing elements include the case that a single light sensing element, moving across the scattered light beam, acts as if a plural number of the light sensing elements. Further, the comparison includes not only the case where a plural number of the light sensing elements produce the same outputs but also the case where they produce different outputs from each other.

Hereby it is desirable that the substantially plural number of the light sensing elements should be disposed optionally around the principal axis of the scattered light beam obtained from the scanned spot without defect as center.

The inspection method in accordance with the present invention is applicable even in case the direction of the principal axis of the scattered light beam remains undeviated while only the distribution of the intensity of the scattered light beam changes which represents a special case of the form of the light beam scattered by the defect on the surface to be inspected or in case there is a plural number of the principal axis of the scattered light beams.

Below, the case of the general form of the scattering that the principal axis of the light beam scattered from the defect on the surface is deviated will be explained.

By means of the inspection method in accordance with the present invention, the detection is carried out by comparing among each other the outputs of a substantially plural number of the light sensing elements receiving the light beam scattered from the scanned spots from spot to spot, so that the inspection method presents the following merits as compared with the conventional method.

A first advantage is that the inspection method in accordance with the present invention is free from the influence of the deviation of the amount of the scanning light beam. Namely, by means of the above mentioned conventional method, the defects and so on are detected by the deviation of the light amount reading the light sensing elements so that the amount of the light beam from the scanned spot changes in case the light amount of the scanning light beam deviates. Thus, there exists a danger that the change of the amount of the light beam from the scanned spot could be detected as defect. On the other hand, by means of the inspection method in accordance with the present invention, the light beam from a single scanned spot reaches a plural number of the light sensing elements in such a manner that the outputs of those light sensing elements are compared with each other. Thus, all the change of the amount of the light beam from the scanned spot works upon all the light sensing elements so that altogether there takes place no influence.

A second advantage of the inspection method in accordance with the present invention is that the direction of the principal axis of the scattered light beam is detected so that the direction of the inclination of the surface presenting defects and so on can be detected.

A third advantage of the inspection method of the present invention is that it is possible to detect the scale of the defect by counting the time during which the direction of the principal axis of the scattered light beam is undetermined.

Further other merits and advantages will be disclosed from the explanation to be made below in accordance with the embodiments of the present invention.

Below the present invention will be explained in accordance with the accompanying drawings, whereby for the sake of the simplicity of the explanation the inspection of an uneven defect on the surface to be inspected will be explained as example. Further, the scattered light beam generally presents a very compicated form due to various factors whereby in the present explanations the scattered light beam is also simplified.

BRIEF EXPLANATION OF THE DRAWINGS

FIG. 1(A) shows the case where there is no defect on the scanned spot while FIG. 1(B) shows the case where there is a defect on the scanned spot.

FIG. 1 shows a side view, FIG. 3 shows a view seen from above, FIG. 4 shows an electric circuit.

FIG. 5 shows the scanning state by a light beam, while FIG. 6 shows a signal processing circuit.

FIG. 26 shows the eighth embodiment of the present invention.

FIG. 27 shows the ninth embodiment of the present invention.

FIG. 28 shows the tenth embodiment of the present invention.

DESCRIPTION OF THE PREFERRED EMBODIMENTS

Figure 1:
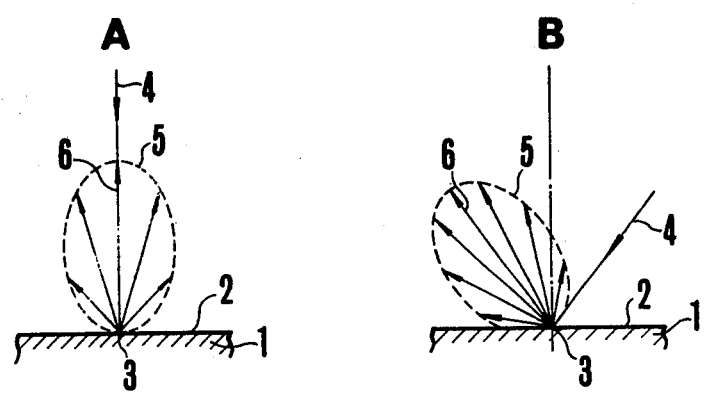
FIG. 1 shows the state of the light beam scattered from the scanned spot, whereby

FIG. 1 shows the reflection characteristics of the scattered light beam reflected from the scanned spot when a narrow scanning beam like a laser beam is projected on the surface to be inspected and free from uneven defects, whereby FIG. 1(A) shows the case when the scanning beam is projected vertically on the surface to be inspected, while FIG. 1(B) shows the case when the scanning beam is projected slantly on the surface to be projected, whereby the scanning beam includes the case when the scanning beam itself moves, the case when the object is moved while the scanning beam is fixed and the combination of both cases. In the drawings, 1 is an object to be inspected, 2 the surface to be inspected, 3 the scanned spot, 4 the scanning beam and the dotted line 5, the scattered light beam reflected from the scanned spot, whereby the intensity and the direction of the scattered light beam is represented in a way of vector. 6 is the line showing the principal axis of the scattered light beam. As is clear from the drawings, the intensity of the scattered light beam is distributed almost in a way of symmetry of rotation around the principal axis of the scattered light beam as center, when the scanning beam is projected vertically or slantly on the surface to be inspected and free of defects. The direction of the principal axis of the light beam scattered from the ordinary surface to be inspected, which is free from the defects such as unevenness and does not possesses any characteristics of the scattering direction coincides with that of the light beam reflected with the same angle as the incident angle of the incident light beam to the surface to be inspected. However, in such a special case that the surface to be inspected has a characteristics of the scattering direction it is necessary to detect the direction of the principal axis for each case because the principal axis of the scattered light beam assumes its own proper direction.

Figure 2:
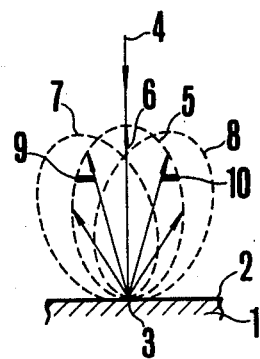
FIGS. 2 to 4 show the first embodiment of the present invention, whereby
Figure 3:
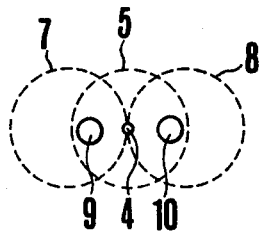

FIGS. 2 and 3 respectively show the inclination of the principal axis of the scattered light beam in case there is a defect at the scanned spot 3 on the surface 2 to be inspected. In case the scanning beam 4 is projected vertically on the surface 2 to be inspected, the direction of the principal axis of the light beam 7, 8 scattered by the uneven defect on the scanned spot is different from that of the light beam scattered from the surface free from defect. The scattered light beam 7 shows that the defect is formed by an incline surface rising along the right direction, while the scattered light beam 8 shows that the defect is formed by an inclined surface rising along the left direction.

In case as mentioned above there is a defect at the scanned spot the direction of the principal axis of the scattered light beam deviates. In this way, it is possible to detect the defect by detecting the deviation of the principal axis of the scattered light beam.

FIGS. 2 and 3 show respectively two light sensing elements 9, 10. These light sensing elements are diametrically disposed to the principal axis 6 of the light beam scattered in case that there is no defect at the scanned spot 3. Thus the output of the light sensing element 7 is same as that of the light sensing element 8 in case that there is no defect at the scanned spot, while there takes place a difference between the outputs in case that there is a defect. For example, in case of the scattered light beam 7 the output of the light sensing element 9 is large, while that of the light sensing element 10 is small. Thus, the case that the output of the light sensing element 9 does not coincide with that of the light sensing element 10 is detected as the case there is some defect on the inspected surface. Further it is possible to determine the direction of the inclination of the surface presenting the defect by detecting which of the light sensing element produces a larger output than the other. Further in the drawings for the sake of the simplicity of the electrical processing the two light sensing elements are disposed symmetrically to the principal axis of the light beam scattered in case there is no defect on the surface 2 to be inspected, whereby the inspection method in accordance with the present invention can be practised no matter whether another axis is used as center or the disposition of the light sensing elements is not symmetrical. Further in case it is desired that the outputs of the two light sensing elements should be made equal to each other when the scattered light beam does not present an ideal distribution as is shown in the drawings, it is sufficient to disposed the light sensing elements at such positions at which their outputs are equal to each other, or to provide variable diaphragms in front of the light sensing elements or variable resistances in the circuits of the light sensing elements.

Figure 4:
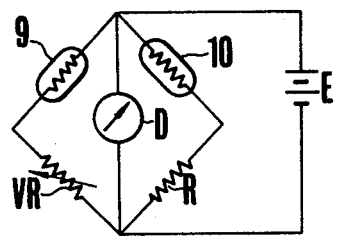
Figure 9:
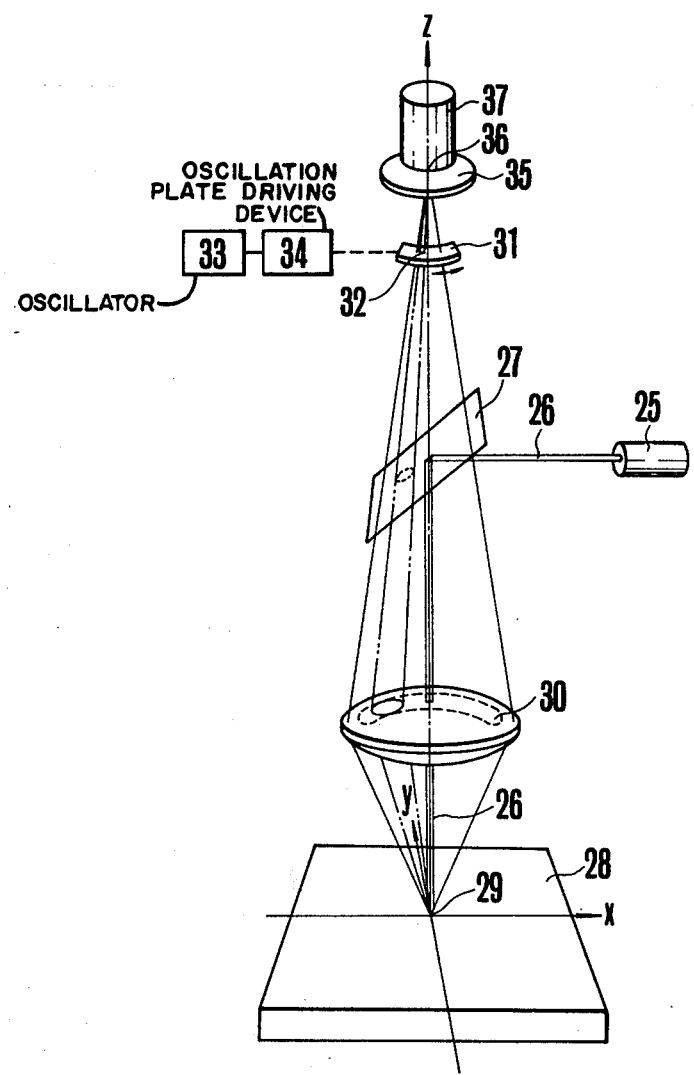
Figure 10:
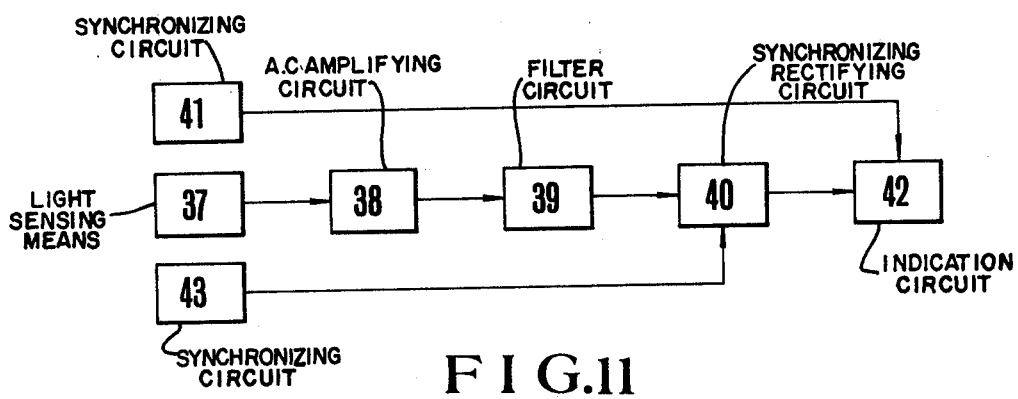

FIG. 4 shows an embodiment of the detecting circuit for the two light sensing elements as shown in FIG. 2. In FIGS. 4, 9 and 10 are the light sensing elements, R a constant resistance, VR a variable resistance, D a galvanometer and E a direct current source, whereby a so called bridge circuit is composed. When the scanned spot 3 is on a surface to be inspected and free from defects, the resistance values of the light sensing elements 9, 10 provided at the optional positions are adjusted by making use of the variable resistance VR in such a manner that no current flows through the galvanometer D. Thus when the light amount reaching the light sensing elements from the scanned spot deviates due to some defect on the surface, the resistance values of the light sensing elements 9, 10 change so as to allow a current to flow through the galvanometer D. Hereby it is possible to estimate the direction and the extent of the defect on the surface by detecting the direction and the intensity of the current flowing through the galvanometer.

Further, the degree of freedom in the disposition of the two light sensing elements can be increased in case the electrical circuit is so designed as to detect the defect by detecting the larger absolute value of the difference between both outputs than a certain determined value instead of detecting the coincidence between the outputs of both light sensing elements.

Figure 5:
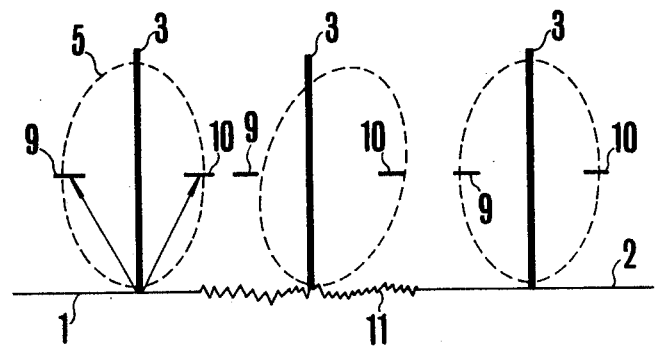
FIGS. 5 and 6 show the second embodiment of the present invention, whereby
Figure 6:
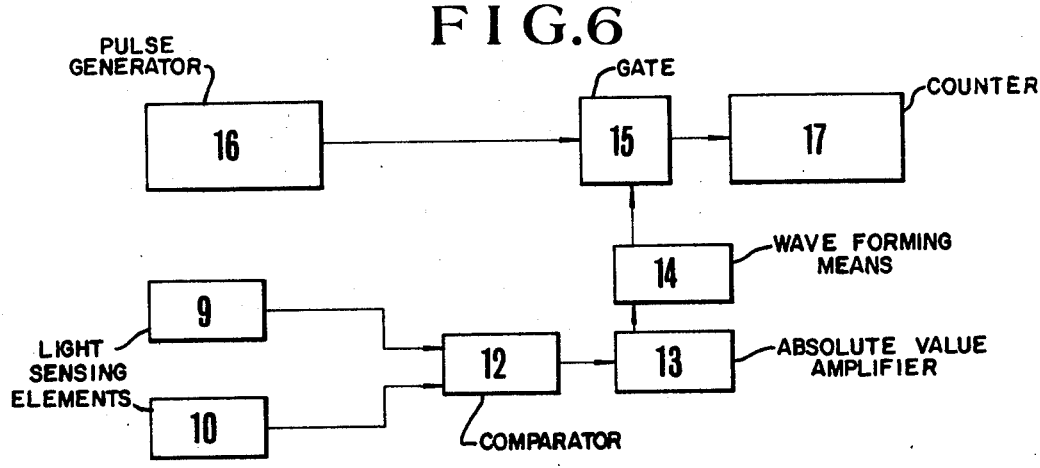

The method for detecting the extent of the defect will be explained in accordance with FIGS. 5 and 6.

11 is the spot on a surface to be inspected, on which spot a defect exists. Now let us suppose that the scanning light beam 4 moves with the light sensing elements 9, 10 from the left to the right in the drawing (see also FIG. 1B). The outputs of the light sensing elements are led into the comparator 12. (FIG. 5). When the scanning beam 4 is scanning the surface free of defect, the output of the comparator is zero. When the scanning beam 4 reaches the spot on which a defect 11 exists, the comparator 14 produces a positive or a negative signal. This positive or a negative signal of the comparator 12 is amplified by means of the absolute value amplifier 13 and led to the gate 15 through the wave forming means 14. Thus the gate 15 is brought into conductive state only when the comparator 12 produces a positive or a negative signal. 16 is a pulse generator. The pulses produced by this generator is being put in the gate 15. The pulse is put in the counter 17 only when the gate 15 is in conductive state, namely the comparator 12 produces a positive or a negative signal. Thus the number of the pulses is counted by the counter 17. Namely the time during which the positive or the negative signal is produced. Connected with the length of this time, the extent of the defect 11 is estimated. When hereby the scanning light beam 4 is produced by a polygon mirror or the like, the speed of the scanning light beam 4 at the center of the object to be inspected differs from that at the circumference, so that a $f$ - Q lens for making the speed of the scanning light beam 4 constant can be used. Further, instead of using a $f$ - Q lens the interval of the pulses produced by the pulse generator 16 can be changed so as to correspond with the position of the scanning light beam 4 to the object to be inspected.

So far the case that the inclination of the principal axis of the scattered light beam is observed by means of the two light sensing element along one direction is explained, while a better result can be obtained when a number of the light sensing elements are arranged so as to carry out the observation along several direction.

In the first and the second embodiment plural number of the light sensing elements are used while in the third embodiment only one light sensing element is used whereby the section of the scattered light beam is scanned.

Figure 7:
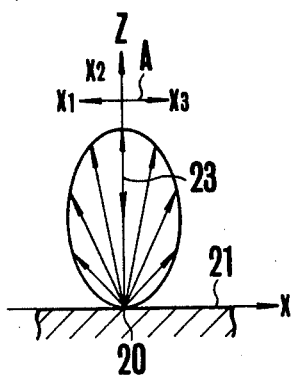
FIGS. 7 to 11 show the third embodiment of the present invention.
Figure 7:
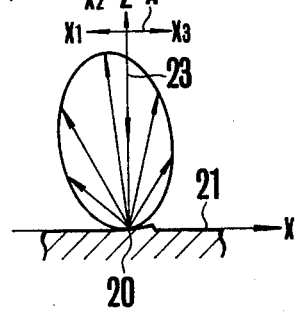
Figure 7:
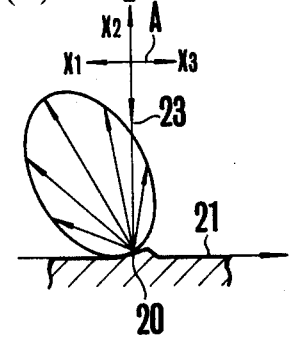
Figure 8:
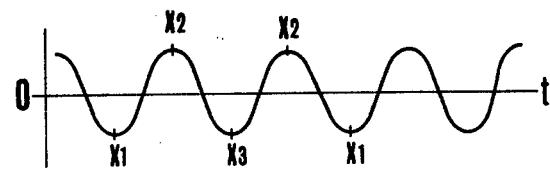
Figure 8:
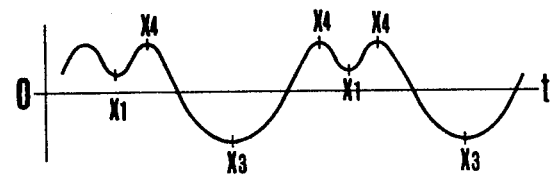
Figure 8:
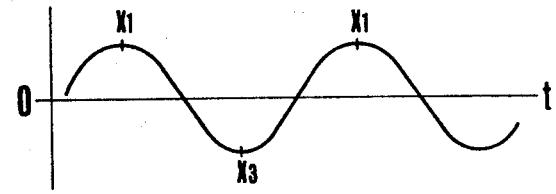

FIG. 7 shows the light beam scattered at the scanned spot on the surface to be inspected, namely the distribution of the amount of the scattered light beam in an optional plane containing the scanned spot in a way of vector. In FIG. 7, the scanned spot 20 is taken for an origin, the direction of the light beam 23 falling vertically on the surface 21 to be inspected as Z-coordinate and the direction vertical to the Z-coordinate in the plane of the paper as x-coordinate. Thus the plane of the paper forms a $x$ - Z plane passing through the origin. In case as is shown in FIG. 7($a$) there exists no defect at the scanned spot 20 on the surface to be inspected, the scattered light beam of the light beam 23 falling vertically on the scanned spot 20 assumes the symmetry of rotation around the Z-coordinate as center. Hereby the peak of the distribution of the amount of the scattered light appears along the direction (in the present case the Z-coordinate) quite opposed to that of the incident light beam. Thus the distribution of the amount of the scattered light beam in the $x$ - Z plane has a peak along the direction of Z-coordinate as is shown in FIG. 7($a$), and is symmetrical with reference to the Z-coordinate. Now in the above mentioned $x$ - Z plane the distribution of the amount of the scattered light beam is continuously detected along a direction parallel to the x-plane (arrow A). When in the present case, a photo detector which oscillate with the frequency $f$ in the span (arrow A), an A.C. output with the frequency $2f$ is obtained as is shown in FIG. 8($a$). Hereby the position of the span is made to correspond with the output by means of the figures $x_1$, $x_2$ and $x_3$.

FIGS. 7($b$) and ($c$) respectively show the case when there is a defect on the surface to be inspected, whereby on the scanned spot 20 there is a defect rising up along the right direction. FIG. 7($c$) shows the case that there is a defect rising up more sharply than the defect of FIG. 7($b$). When similarly to the above mentioned case, the light amount is detected for the span A in $x$ - Z plane, the output in case of FIG. 7($b$) assumes the form as shown in FIG. 8($b$) while the output in case of FIG. 7($c$) assumes the form as shown in FIG. 8($c$). When in cases the detection is carried out continuously for the span A by means of a photo detector which oscillates with the frequency $f$, the A.C. output also with the frequency $f$ can be obtained regardless of the wave form of the output signal.

Namely, when there exists no defect on the surface a signal with a frequency twice as large as that $f$ of the photo detector can be obtained, while when there exists a defect on the surface a signal with the same frequency as that $f$ of the photo detector can be obtained.

FIG. 9 shows an embodiment in accordance with the principle of FIGS. 7 and 8 in perspective view. In FIG. 9, 25 is a source of light such as laser, 26 the incident light beam coming from the light source 25, 27 a semipermeable mirror, 28 the surface to be inspected and 29 the scanned spot. 30 is the condenser lens for condensing the light beam scattered at the scanned spot 29. A concave lens can be used instead of the condenser lens. 31 is an oscillation plate presenting an opening 32, and being oscillated with a frequency $f$ by means of the oscillation plate driving device 34 which is driven by the oscillator 33 which oscillates with the frequency $f$. This oscillation plate 31 can be placed in front of the condenser lens 30. 35 is the diaphragm plate presenting an opening 36, while 37 is a light sensing element.

The light beam 26 coming from the light source is reflected by means of the semipermeable mirror 27 and projected vertically to the scanned spot on the surface to be inspected along the Z-coordinate through the condenser lens 30. A part of the light beam scattered at the scanned spot 29 is condensed by means of the condenser lens 30 and focussed on the diaphragm plate 35 through the semipermeable mirror 27 and the opening 32 of the oscillation plate 31. Then the light beam having passed through the opening 36 of the diaphragm plate 35 is detected by the photo sensing means 37.

FIG. 10 shows an electrical circuit for electrically processing the signal detected by the above mentioned light sensing means 37. 38 is the A.C. amplifying circuit, 39 a filter circuit, 40 a synchronizing rectifying circuit, 41 an oscillation circuit which produces pulses with a frequency $f$ and 42 and indication circuit. Hereby this indication circuit is set respectively reset by means of the pulses produced by the oscillation circuit. Namely, the measured light value during one oscillation of the oscillation opening is successively indicated. 41 is the synchronizing circuit which produces pulses at every $\frac{1}{2}f$ second for the frequency $f$ of the above mentioned oscillation circuit, producing pulses synchronized with the state of the opening 32 of the oscillation plate so as to control the synchronizing rectifying circuit 40. In the explanation below the pulse is supposed to be produced at the beginning $x_1$ of the span A and at the end $x_2$. The electrical circuit will be explained in accordance with the case of FIG. 7(*b*).

Figure 11:
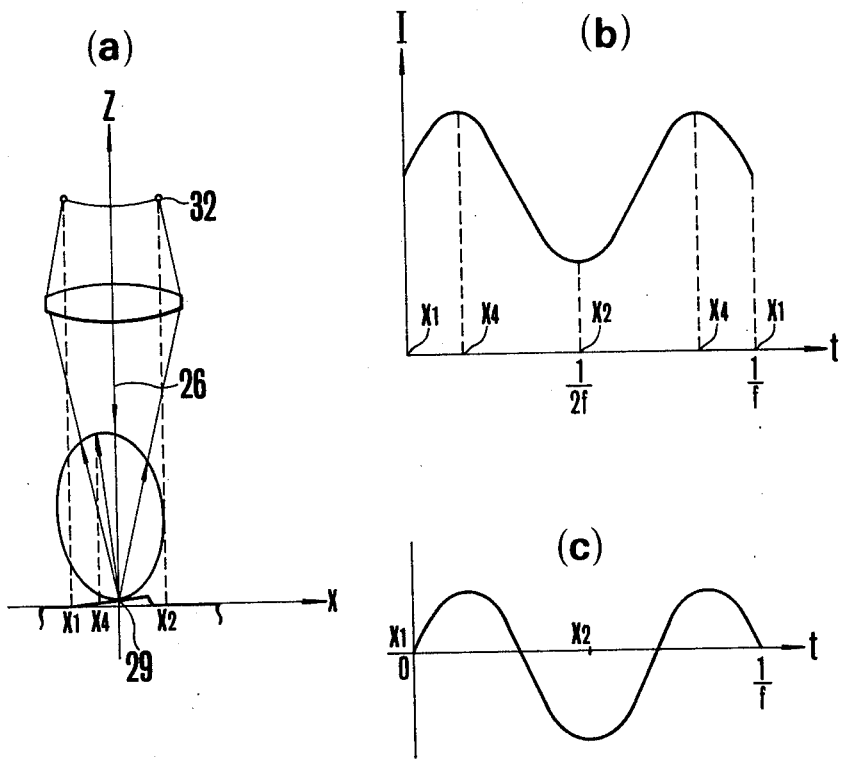

FIG. 11(*a*) shows the scattering characteristics in case of FIG. 7(*b*) and the measuring instrument. The distribution of the amount of the scattered light beam in the $x$ - Z plane including the scanned spot as origin is inclined to the left because there is a defect rising up along the right direction.

The position at which the oscillation opening 32 comes fully to the left is indicated with $x_1$, while the position at which the oscillation opening 32 comes fully to the right is indicated with $x_2$. Hereby the oscillation opening 32 is so designed to oscillate with the frequency $f$ around the Z-coordinate right and left by the same amount.

Now the synchronizing device 41 is set in such a manner that when the oscillation circuit 32 assumes the position $x_1$ the synchronizing device 41 produces pulses. While the oscillation opening carries out one oscillation $x_1 \rightarrow x_2 \rightarrow x_1$ with $1/f$ sec., the light beam having passed through the opening 32 is detected as A.C. signal containing a component with a frequency $f$ as is shown in FIG. 11(*b*). In FIG. 11(*b*), the ordinate shows the light amount I while the abscissa shows the time $t$. As explained above, the signal of the synchronizing device 41 is synchronized with the position $x_1$ of the oscillation opening 32, so that the coordinate corresponds with the abscissa in such a manner that after $\frac{1}{2}f$ sec. the opening 32 assumes the position $x_2$, and after $1/f$ sec. the position $x_1$. In this way, the position of the opening 32 can be obtained.

The output detected by the light sensing element 37 is amplified by means of the A.C. amplifying circuit 38 as is shown in FIG. 11(*c*) and led to the filter circuit 39.

When the output of the filter circuit 39 is directly indicated in the synchroscope or the like of the indication circuit 42, being synchronized with the signal from the synchronizing circuit 41, such wave form as is shown in FIG. 11(*c*) is indicated in the cathode ray tube, whereby by observing the distribution of the amount of the scattered light beam directly with the eyes, the defect and its direction at the scanned spot on the surface to be inspected can be detected.

In case it is desired that the output of the filter circuit 39 should be indicated analogically, the output of the filter circuit 39 is put in the rectifying circuit 40 as is shown in FIG. 10. This rectifying circuit 40 is controlled in its operation by means of the pulses of the oscillation circuit, whereby the output of the filter circuit 39 between $x_1$ and $x_2$ in FIG. 7 is integrated. This integrated value is indicated by the indication circuit. When there exists no defect on the surface 21 (FIG. 7(*a*)) the integrated value is zero as is clear when the situation between $x_1$ and $x_3$ in FIG. 8 is observed. However, in case of FIG. 7(*b*) and (*c*), the integrated value is positive. Hereby its extent depends upon the inclination of the principal axis of the scattered light beam. The sign of the integrated value depends upon the direction of the inclination. Thus it is possible to detect the defect, its extent and its direction by estimating the integrated value.

The above mentioned detecting circuit is made to detect, beside the defect, its direction too, whereby in case it is desired that only the defect could be detected it is sufficient to provide such a filter circuit as interrupts or allows to pass either of the frequencies $f$ or $2f$, and to detect the output of the filter circuit.

Figure 12:
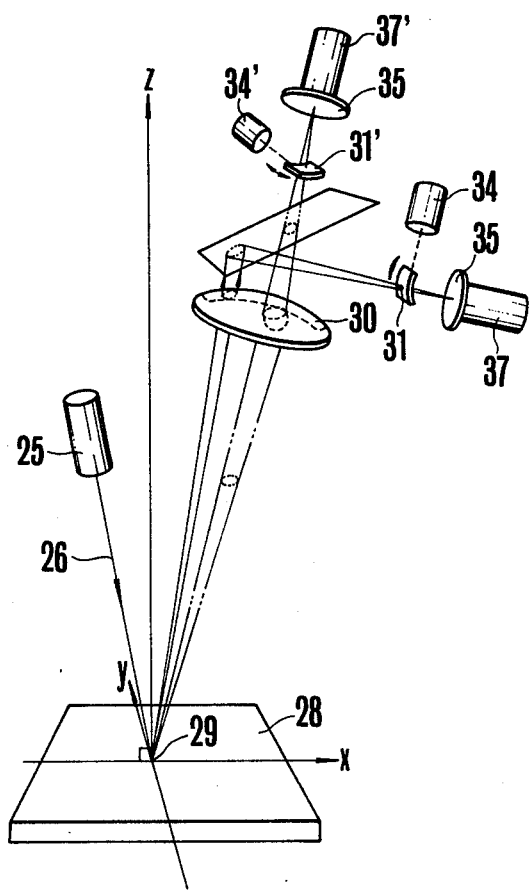
FIG. 12 shows the fourth embodiment of the present invention.

FIG. 12 shows the fourth embodiment of the present invention in perspective view. In case of this embodiment it is possible to detect the state of the defect on the surface to be inspected more precisely by providing a plural number of the oscillation plates 31. In FIG. 12, the same devices as those in the embodiment shown in FIG. 9 posesses the same figures.

The light beam emitted from the light source 25 is scattered at the scanned spot 29 on the surface 28 to be inspected. The scattered light beam is condensed by the condenser lens 30, whereby the one part is reflected by the semi-permeable mirror 27 and led to the first detecting system while the other part passes through the semi-permeable mirror 27 and is led to the second detecting system.

The oscillation plate 31 in the first detecting system and the oscillation plate 31' in the second detecting system are so designed that they oscillate vertically to each other. Thus from the outputs of the light sensing means 37, 37 of both detecting systems the variation of the amount of the light beam scattered on the planes including the scanned spot 29 and crossing vertically to each other out of the light beam scattered at the scanned spot can be detected. When the above mentioned synchronizing circuits 41, 43 are provided in those light detecting systems in such a manner that the output is detected by means of the electrical circuit shown in FIG. 10, the direction of the defect on the surface to be inspected can be detected more precisely as compared with the light detecting system of one series. In accordance with the fourth embodiment a light detecting system of two series whereby the more light detecting systems are provided the more precise measurement can be carried out.

Similarly to the case of the above mentioned embodiment the angle of the light beam falling on the surface to be inspected is not bound by the surface to be inspected at all, whereby further any plane including the scanned spot serves as the oscillation plane for detecting the scattered light beam.

By properly setting the range of the position which the scattered light beam reaches, namely the oscillation position of the oscillation opening, it is possible that the detection signal of the scanned spot free from the defect presents a component with the frequency $f$.

Further, it is possible to detect only a specified state of the surface to be inspected when such a filter circuit as detects the light beam scattered on the surface to be inspected and in a specified state and allows a component with a specified frequency out of the output to pass is provided in advance.

Figure 13:
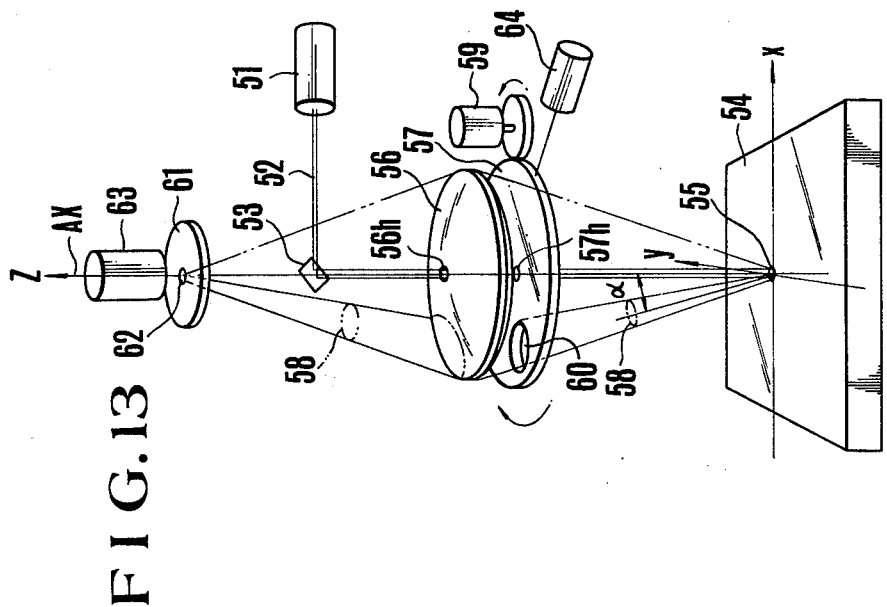

FIG. 13 shows the fifth embodiment of the present invention. In the drawing, the light beam 52 from a source 51 of light such as laser is reflected by the reflecting mirror 53 arranged on the optical axis AX (Z axis in FIG. 13) of the optical system provided vertically to the object 54 to be inspected and projected vertically to the object 54 to be inspected through the condenser lens 56 and the openings (56h, 57h) provided at the center of the rotary plate 57. A part 58 of the light beam scattered on the scanned spot 55 is led through the opening 60 rotating along a doughnut-shaped orbit and being provided on the circumference of the rotary plate 57 rotated around the optical axis AX as center by means of the driving equipment 59 and reaches the light sensing element 63 through the condenser lens 56 and the opening 62 on the diaphragm plate 61 provided on the optical axis AX. 64 is a synchronizing device, producing a synchronizing signal with the rotation of the rotary plate 57. In FIG. 13, the light beam to be detected by the light sensing device 63 through an opening 60 of the rotary plate 57 is such a scattered light beam has a central beam at a position making an angle $\alpha$ to the optical axis AX (axis Z).

Figure 14:
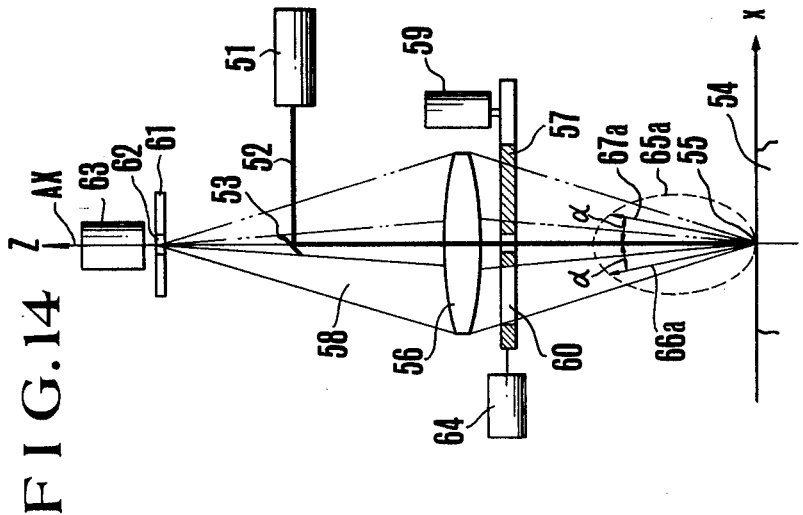
FIGS. 13 to 21 show the fifth embodiment of the present invention.

FIG. 14 shows a front section of FIG. 13. The dotted line 65a in FIG. 14 shows the relation between the direction of the scattered light beam from a scanned spot 55 free from defect and its intensity, namely the scattering characteristics in a way of vector. In case of an equipment consisting of an optical system in which the light beam from a light source reaches the object to be inspected vertically along the optical axis AX as is shown in FIG. 14, the scattering characteristics of the scattered light beam from the scanned spot free from defect is nearly of symmetry of rotation around the principal axis of the scattered light beam (in the present case AX axis). The light beams (66a, 67a) scattered making an angle $\alpha$ to the optical axis have the same intensity.

Figure 15:
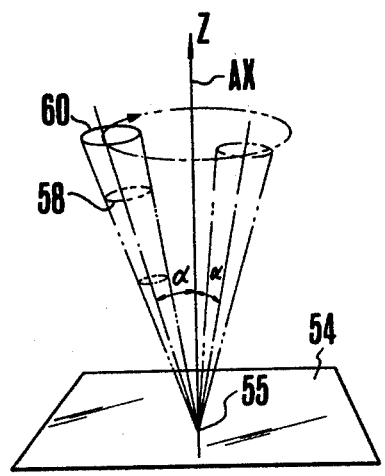
Figure 17:
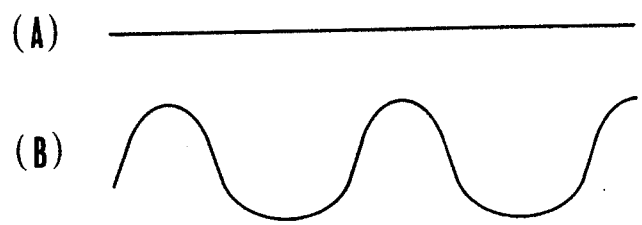

Now let us suppose that the light beam reflected at the scanned spot free from defect and reaching the light sensing means through the opening 60 of the rotary plate 57 as is shown in FIG. 14 be a scattered light beam making an angle $\alpha$ to the optical axis AX. Namely as is shown in FIG. 15 the center of the opening 60 of the rotary plate rotates around the optical axis AX as center, making an angle $\alpha$ to the optical axis constant. The then detected signal of the light sensing means 63 is an ordinary D.C. output as is shown in FIG. 17, because the opening 60 of the rotary plate 57 runs in a plane in which the distribution of the amount of the scattered light beam is equal. (Hereinafter called vector reflecting plate.)

Figure 16:
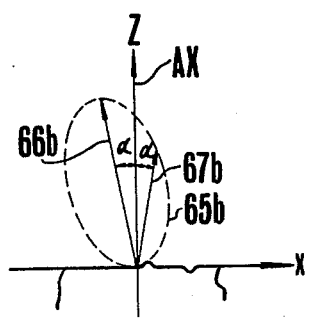
Figure 18:
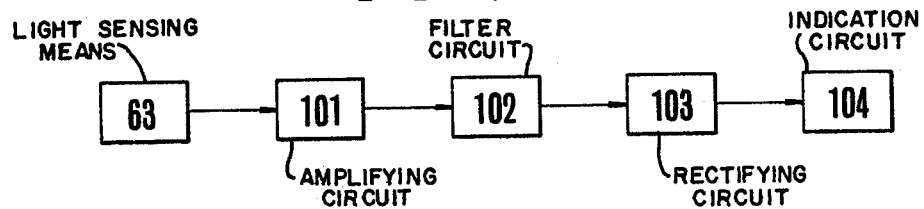

On the other hand, in case there is an irregularity such as defect, inclination and so on at the spot to be scanned, the principal axis of the scattered light beam deviates. An example of the vector of the scattering characteristics in this case is shown with 65b in FIG. 16. At 65b in FIG. 16 the principal axis of the scattered light beam is inclined toward the left so that the scattered light beams (66b, 67b) making an angle $\alpha$ to the optical axis AX are not equal in the intensity. Thus when the light beam scattered on a surface with defect is detected by the light sensing means 63 through the rotary plate 57 of such a device as is shown in FIG. 15, a detected signal containing a component of the rotation number of the rotary plate 57 and a component of the frequency due to the defect on the surface to be inspected is obtained as is shown in FIG. 17(B). The signals (A) and (B) in FIG. 17 are determined by a circuit shown in FIG. 18. In FIG. 18, 63 is the light sensing means, 101 the amplifying circuit for amplifying the current from the light sensing means, 102 the filter circuit which allows only the frequency component due to the defect on the surface out of the frequency components of the detected signal to pass through, checking other noises not necessary for the inspection, 103 the rectifying circuit and 104 the indication circuit. Thus by detecting whether in the above mentioned circuit the detected signal contains the frequency component due to the defect on the surface and the rotation number of the rotary plate 57 or not, whether there is a defect on the surface or not can be detected, while the extent of the defect can be estimated by the output of the light sensing means.

Figure 19:
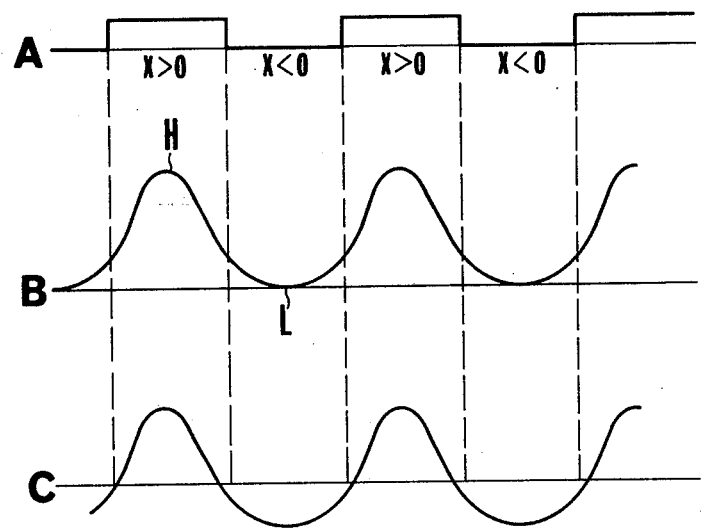
Figure 20:
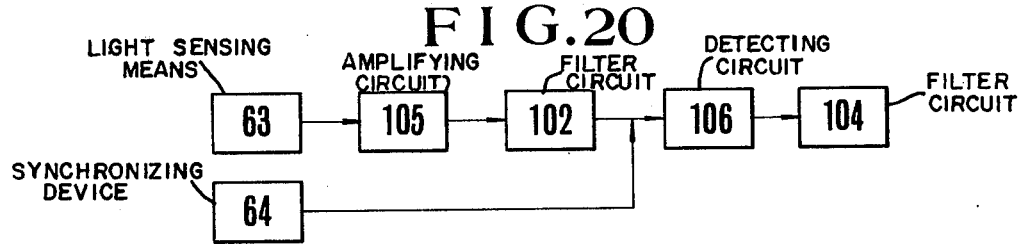

Further such a synchronizing device 64 as produces such gate signals as shown in FIG. 1A only when the opening 60 on the rotary plate 57 passes the positive domain of the $x$ component in the $x, y, Z$-coordinate shown in FIG. 13 is provided. Supposing that the optical axis of the light beam scattered due to the defect at the scanned spot 55 is inclined along the positive direction of the $x$-axis, the intensity of the current detected by the light sensing means 63 is as is shown by the curve in FIG. 19 B. This detected current is put in the electrical circuit shown in FIG. 20. The detected current from the light sensing means 63 is amplified by the amplifying circuit 105 into A.C. current in which a zero level is set in such a manner that the energy value in the positive domain is equal to that in the negative domain, and then other noises than the frequency equal to the rotation number of the rotary plate 57 is eliminated by the filter circuit 104 whereby the passed frequency component is led into the detecting circuit 106 with the synchronizing signal (FIG. 19 A). In the detecting circuit 106 the curve shown in FIG. 19 C is rectified in the domain $x > 0$ in such a manner that the positive signal is led into the indication circuit so as to be indicated. In this way, it is shown that the scattered light beam is inclined along the positive direction of the X axis, in such a manner that the direction of the defect on the surface is judged. By providing a synchronizing device in this way, the direction of the scattered light beam can be judged from the sign of the output from the detecting circuit while the extent of the defect can be judged by the indicated amount.

Figure 21:
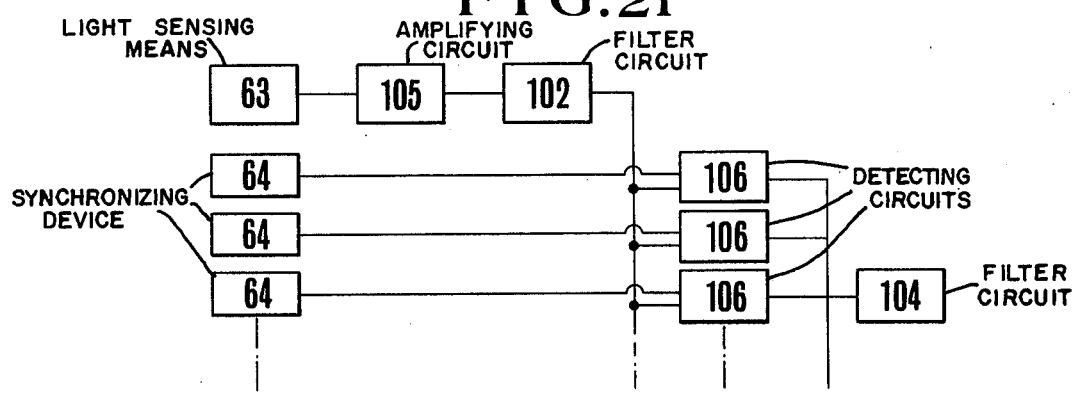

Further by providing a plural number of the synchronizing circuits (FIG. 21), the irregularity of the scanned spot is divided in a plural number of the components at the same time by a single equipment in such a manner that the kind and the extent of the defect on the surface can be detected by analysing the detected result.

Figure 22:
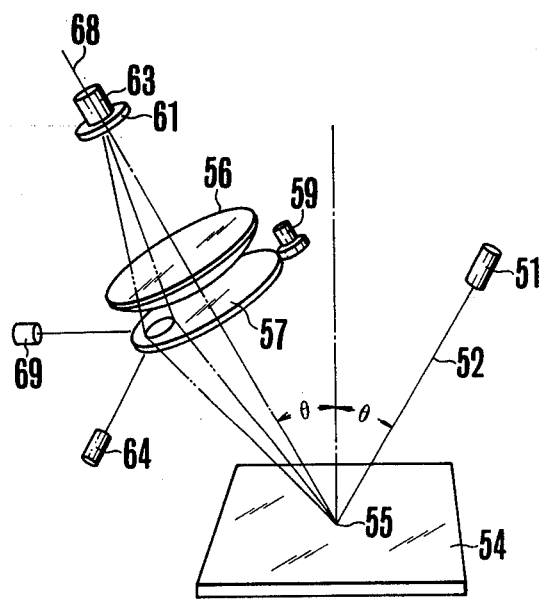
FIGS. 22 to 24 show the sixth embodiment of the present invention.

In the above mentioned fifth embodiment, the light beam is projected vertically to the object to be inspected, while as is shown in FIG. 22 a light beam presenting some incident angle can also be applied. When in this case the optical axis 68 of the detecting optical system is set along the principal axis of the light beam 52 scattered on the reflecting surface from defect on the surface, the above mentioned operation is possible.

With the variation of the incident angle of the light beam projected to the surface to be inspected the scattering characteristics varies, whereby it is possible that the scattering characteristics be not of the symmetry of rotation around the principal axis of the scattered light beam as center as in case of vertical projection so that it is possible that a D.C. current as shown in FIG. 17 A could not be obtained even in case there is no defect on the scanned spot. In this case, it is necessary to detect the reflecting characteristics on the scanned spot free from defect at every projection angle by means of a detecting optical system (56, 57, 61, 63) in advance.

Figure 23:
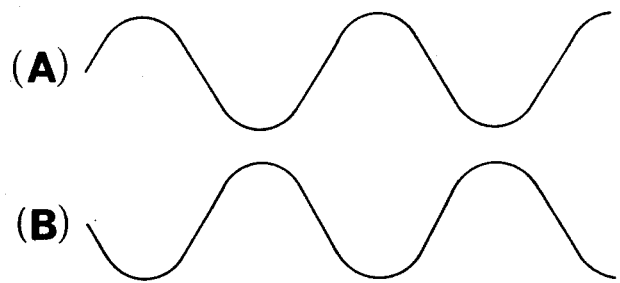
Figure 24:
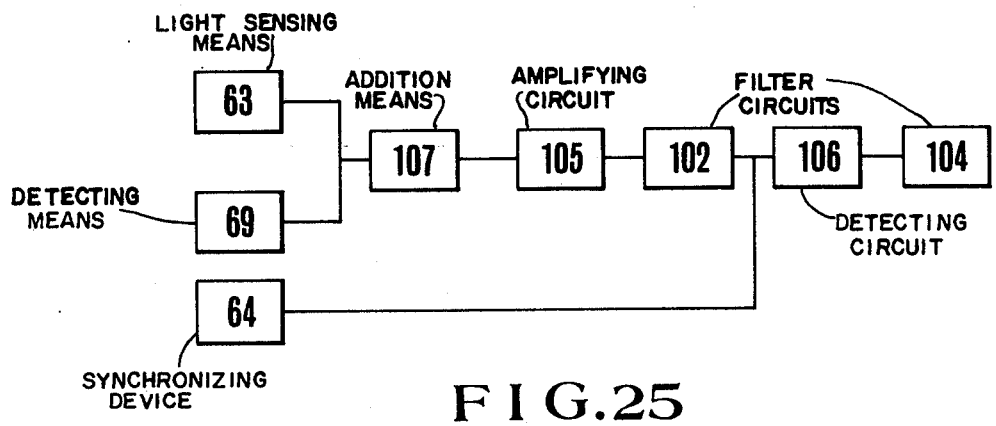

When an output shown in FIG. 23 (A) is obtained in case the light beam scattered from the scanned spot free from defect out of the light beam projected at an incident angle $\theta$ in FIG. 22, a detecting means 69 which produces an output as shown in FIG. 23 (B) reversedly to the output shown in FIG. 23 (A) with the rotation of the rotary plate 57 is provided. FIG. 24 shows a circuit for processing the above output, whereby the output from the light sensing means 63 and that from the detecting means 69 are composed in the addition means 107 and led to the amplifying circuit 105. Thus when the scanned spot is free from defect, the output from the light sensing means 63 and that from the detecting means 69 are compensated with each other in such a manner that a D.C. output as is shown in FIG. 17 (A) is obtained, whereby a similar measurement is possible as in case the scattering characteristics of the above mentioned scattered light beam is of symmetry of rotation around the principal axis of the scattered light beam as center.

Figure 25:
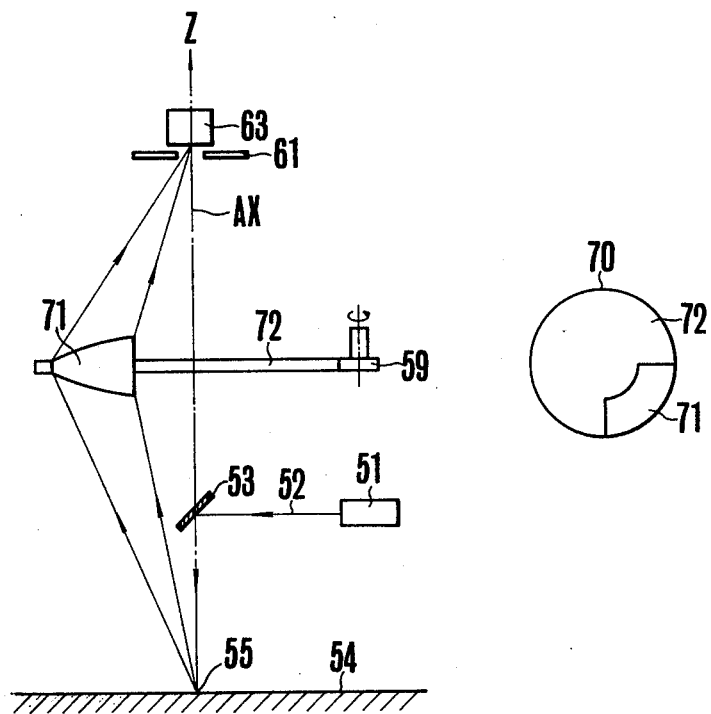
FIG. 25 shows the seventh embodiment of the present invention.

FIG. 25 shows the front section of the seventh embodiment of the present invention. The same components as in the fifth and the sixth embodiments present the same figures. The light beam 52 from the light source 51 is projected vertically to the scanned spot 55 on the object to be inspected, by means of the reflecting mirror 53 arranged on the optical axis AX (Z axis), and immediately reflected and scattered. 70 is a rotary member consisting of a disc of a non-transparent member 72 with a notch in which notch a part 71 of a lens is inserted, and rotated around the optical axis AX as center by means of a driving equipment 59. Thus only the light beam having passed through the lens part 1 in the rotary member 70 out of the above mentioned light beam is led to the light sensing means 63 placed in the neighborhood of a plane conjugate to the above mentioned scanned spot with reference to the lens part 71. In this equipment a rotary member consisting of the rotary plate 57 of the fifth embodiment and of a condenser lens 56 is used so that the light beam reaching the light sensing means 63 always passes the lens part 71 so as to make the optical measuring condition constant so that the influence of the aberration of the lens or the stain sticking to the lens is exempted.

FIG. 26 shows a front section of the eighth embodiment of the present invention. In FIG. 26, 73 is a plane reflecting mirror fixed on the circumference of a rotary disc 75 having a center of rotation on the optical axis AX of the optical system of the seventh embodiment and being rotated by means of a driving means 59, so as to reflect a part 58 of the scattered light beam from the scanned spot 55, 74 the plane mirror provided on the optical axis AX and fixed by the arm 75′ on the rotary disc 75, being opposed to the plane reflecting mirror 73 so as to lead the light beam reflected by the plane reflecting mirror 73 always to the condenser lens 56. The light beam 52 from the light source 51 is projected vertically to the scanned spot 55 on the surface 54 to be inspected by means of the reflecting mirror provided on the optical axis AX and scattered. Out of the scattered light beam, the light beam reflected by the above mentioned plane reflecting mirror 73 is reflected by the plane reflecting mirror 74 along the optical axis AX and led to the light sensing means 63 through the condenser lens 56. In this case, a concave mirror can be used instead of the plane reflecting mirror 74 so as to lead the light beam directly to the light sensing means 63 without using the condenser lens 56.

In case of the seventh embodiment in FIG. 25 as well as the eighth embodiment in FIG. 26 the light beam for inspecting the object is projected vertically while as is explained in accordance with FIG. 22 the light beam can be projected slantly.

In the fifth embodiment to the eighth embodiment the light amount is detected by a single light sensing element. As compared with the case a number of the light sensing elements are arranged on an equi-vector plane for detecting the light amount, the above mentioned system is profitable because there is no difference among the response characteristics of the light sensing element.

FIG. 27 shows the nineth embodiment of the present invention. 76 is a polygon mirror for scanning which optically scanns the object to be inspected along the direction of the movement of the object (arrow 78) and the vertical direction (arrow 79). 77 is a concave mirror designed in such a manner that the point at which the light beam reaches the above mentioned polygon mirror 76 and the point at which the light beam, being scanned by the polygon mirror, reaches the scanned spot are conjugate to each other. The light beam 52 from the light source 51 reaches the polygon mirror 76 along the optical axis AX by means of the reflecting mirror 53 provided on the optical axis AX, is reflected by the polygon mirror 76 and further by the concave mirror 77, projected vertically to the scanned spot and scattered. The scattered light beam is caught by the concave mirror 77 and condensed on the polygon mirror 76 at a position conjugate to the scanned spot 55 with reference to the concave mirror. Thus the light beam reflected on a spot on the polygon mirror 76 and reaching the detecting optical system (56, 57, 61, 63) becomes indentical with the light beam reflected on the scanned spot so that the scanning. The rotary plate 57 rotates at a very high speed as compared with the polygon mirror 76 so that the light beam reflected on the scanned spot 55 can be detected before the relative position of the polygon mirror 76 to the object 54 to be inspected changes.

In the fifth embodiment to the nineth embodiment, a widely adopted rotary encoder can be used as synchronizing device 64, while a certain desired pattern is provided on the circumference equally devided of the rotary disc 56 can be detected.

In case of a detecting means 68 which produces an output signal corresponding to the rotation amount of the rotary disc 56, a pattern which produces a certain determined signal similarly to the above mentioned synchronizing means 64 is provided on the circumference of the rotary disc 56 and detected by the senser.

Further, the shape of the scanned spot and that of the opening 62 of the diaphragm plate 61 can be chosen freely so as to meet the purpose of the inspection while their sizes can also be chosen freely.

Further, in the above mentioned embodiment, the equi-vector reflecting plane of the scattered light beam is supposed to be of symmetry of rotation, whereby even if the scattering characteristic is of symmetry of rotation, in reality it is very seldom that the equi-vector plane of the scattered light beam be of symmetry of rotation and therefore it is necessary to carry out a rotation scanning in order to scann the equi-vector reflecting plane in accordance with the reflecting characteristics.

Further, in case the reflecting characteristics is of symmetry of rotation even if the surface to be inspected is free from defect, it is possible to carry out a similar measurement as the above mentioned method by providing a means capable of detecting the equi-vector reflecting plane whose reflecting characteristics of scattered light beam has been detected in advance, for example a slit plate 81 presenting a slit 80 of a certain desired pattern of the equi-vector reflecting plane as is shown in FIG. 28 close to the rotary plate. On the other hand, in case the central axis of symmetry of rotation does not coincide with the principal axis of the scattered light beam despite that the light beam reflected from the scanned spot free from defect present a reflecting characteristics of symmetry of rotation, it is possible to scan the equi-vector reflecting plane by translating the optical axis of the inspection optical system in accordance with the present invention so as to coincide with the above mentioned central axis of symmetry of rotation.

The surface inspection devices according to the fifth to the tenth embodiments are quite profitable because the scattered light beam reflected on a scanned spot on the surface to be inspected is measured by light sensing means provided along a plural number of directions in the scattered light beam so as to compare their output with each other, whereby there is no influence due to the variation of the light amount due to the disturbance from without.

What is claimed is:

1. A method for inspecting a defect of an object comprising the steps of:
projecting a narrow beam to the object, whereby a scattered light beam takes place from the spot on the object projected with the beam;
scanning this scattered light beam for inspection along a certain predetermined circular line to obtain a serial DC output signal when a defect does not exist at the scanned spot and to obtain a serial AC output signal when a defect exists at the scanned spot; and
detecting whether there exists a defect or not by determining whether the output signal is DC or AC.

* * * * *

UNITED STATES PATENT OFFICE
CERTIFICATE OF CORRECTION

Patent No. 4,097,160          Dated   June 27, 1978

Inventor(s)   Masamichi Yataki, et al

It is certified that error appears in the above-identified patent and that said Letters Patent are hereby corrected as shown below:

In the heading of the Patent [75] and [30] should read as follows:

[75] Inventors: Masamichi Yataki, Tokyo; Hideyo Takahata, Yokohama; Norio Simomura, Kanagawa-ken; all of Japan

[30] Foreign Application Priority Data

Oct. 7, 1974   Japan..............49-115323
Oct. 2, 1974   Japan..............49-113610
Sept. 6, 1974  Japan..............49-102679

Signed and Sealed this

Fifth Day of December 1978

[SEAL]

Attest:

RUTH C. MASON
Attesting Officer

DONALD W. BANNER
Commissioner of Patents and Trademarks